United States Patent
Tehrani et al.

(10) Patent No.: US 10,821,010 B2
(45) Date of Patent: Nov. 3, 2020

(54) METHOD OF MAKING A MULTI-STRAND IMPLANT WITH ENHANCED RADIOPACITY

(71) Applicant: DEPUY SYNTHES PRODUCTS, INC., Raynham, MA (US)

(72) Inventors: Ramin Tehrani, Hialeah, FL (US); Robert Slazas, Miami, FL (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 0 days.

(21) Appl. No.: 16/046,428

(22) Filed: Jul. 26, 2018

(65) Prior Publication Data

US 2018/0333281 A1 Nov. 22, 2018

Related U.S. Application Data

(62) Division of application No. 14/469,862, filed on Aug. 27, 2014, now Pat. No. 10,206,796.

(51) Int. Cl.
| | |
|---|---|
| *A61F 2/86* | (2013.01) |
| *A61F 2/06* | (2013.01) |
| *A61F 2/07* | (2013.01) |
| *D03D 3/02* | (2006.01) |
| *D04C 1/02* | (2006.01) |

(Continued)

(52) U.S. Cl.
CPC ............. *A61F 2/86* (2013.01); *A61B 34/10* (2016.02); *A61B 90/39* (2016.02); *A61F 2/06* (2013.01); *A61F 2/07* (2013.01); *D03D 3/02* (2013.01); *D04C 1/02* (2013.01); *D04C 1/06* (2013.01); *A61F 2250/0032* (2013.01); *A61F 2250/0098* (2013.01); *D10B 2509/06* (2013.01)

(58) Field of Classification Search
CPC .... D04C 1/02; D04C 1/06; D04C 1/12; A61F 2/86
See application file for complete search history.

(56) References Cited

U.S. PATENT DOCUMENTS

| | | | | |
|---|---|---|---|---|
| 4,332,278 A | * | 6/1982 | Lalikos ................. | D04C 3/12 138/127 |
| 4,610,688 A | | 9/1986 | Silvestrini | |

(Continued)

FOREIGN PATENT DOCUMENTS

| | | |
|---|---|---|
| CN | 101234046 A | 8/2008 |
| CN | 102271620 A | 12/2011 |

(Continued)

OTHER PUBLICATIONS

MIG-Welding.Co.UK; Excerpt from with comment of Jun. 29, 2011 on pictures of welds.

(Continued)

*Primary Examiner* — Shaun R Hurley
(74) *Attorney, Agent, or Firm* — Troutman Pepper Hamilton Sanders LLP

(57) ABSTRACT

Methods of making an implant for medical use, having a body formed of a plurality of single strands of a first material. The body further includes at least one multi-strand of radiopaque material incorporated among the single strands, the multi-strand having at least two side-by-side filaments of radiopaque material that lie substantially contiguous to each other over substantially the entire length of the multi-strand.

16 Claims, 3 Drawing Sheets

(51) Int. Cl.
*D04C 1/06* (2006.01)
*A61B 34/10* (2016.01)
*A61B 90/00* (2016.01)

(56) References Cited

U.S. PATENT DOCUMENTS

| | | | |
|---|---|---|---|
| 4,754,685 A * | 7/1988 | Kite | D04C 1/02 87/9 |
| 5,064,435 A | 11/1991 | Porter | |
| 5,282,824 A | 2/1994 | Gianturco | |
| 5,330,500 A | 7/1994 | Song | |
| 5,382,259 A | 1/1995 | Phelps et al. | |
| 5,387,235 A | 2/1995 | Chuter | |
| 5,423,849 A | 6/1995 | Engelson | |
| 5,476,508 A | 12/1995 | Amstrup | |
| 5,522,881 A | 6/1996 | Lentz | |
| 5,549,662 A | 8/1996 | Fordenbacher | |
| 5,556,413 A | 9/1996 | Lam | |
| 5,601,593 A | 2/1997 | Freitag | |
| 5,609,627 A | 3/1997 | Goicoechea | |
| 5,645,558 A | 7/1997 | Horton | |
| 5,662,622 A | 9/1997 | Gore | |
| 5,702,418 A | 12/1997 | Ravenscroft | |
| 5,725,549 A | 3/1998 | Lam | |
| 5,728,131 A | 3/1998 | Frantzen | |
| 5,755,772 A | 5/1998 | Evans et al. | |
| 5,769,887 A | 6/1998 | Brown | |
| 5,776,161 A | 7/1998 | Globerman | |
| 5,817,126 A | 10/1998 | Imran | |
| 5,849,037 A | 12/1998 | Frid | |
| 5,851,217 A | 12/1998 | Wolff | |
| 5,899,935 A | 5/1999 | Ding | |
| 5,916,235 A | 6/1999 | Guglielmi | |
| 5,916,264 A | 6/1999 | Von Oepen | |
| 5,961,546 A | 10/1999 | Robinson et al. | |
| 6,010,529 A | 1/2000 | Herweck | |
| 6,015,432 A | 1/2000 | Rakos et al. | |
| 6,033,436 A | 3/2000 | Steinke | |
| 6,036,725 A | 3/2000 | Avellanet | |
| 6,051,020 A | 4/2000 | Goicoechea | |
| 6,099,559 A | 8/2000 | Nolting | |
| 6,110,198 A | 8/2000 | Fogarty | |
| 6,123,722 A | 9/2000 | Fogarty et al. | |
| 6,123,723 A | 9/2000 | Konya et al. | |
| 6,152,956 A | 11/2000 | Pierce | |
| 6,161,399 A * | 12/2000 | Jayaraman | D04B 1/14 623/1.5 |
| 6,165,213 A | 12/2000 | Goicoechea | |
| 6,168,621 B1 | 1/2001 | Vrba | |
| 6,176,875 B1 | 1/2001 | Lenker | |
| 6,264,683 B1 | 7/2001 | Stack et al. | |
| 6,280,465 B1 | 8/2001 | Cryer | |
| 6,319,278 B1 | 11/2001 | Quinn | |
| 6,325,823 B1 | 12/2001 | Horzewski | |
| 6,348,066 B1 | 2/2002 | Pinchuk et al. | |
| 6,409,755 B1 | 6/2002 | Vrba | |
| 6,488,702 B1 | 12/2002 | Besselink | |
| 6,612,012 B2 | 9/2003 | Mitelberg et al. | |
| 6,626,936 B2 | 9/2003 | Stinson | |
| 6,635,080 B1 | 10/2003 | Lauterjung et al. | |
| 6,673,106 B2 | 1/2004 | Mitelberg | |
| 6,699,277 B1 | 3/2004 | Freidberg et al. | |
| 6,740,113 B2 | 5/2004 | Vrba | |
| 6,673,107 B1 | 6/2004 | Brandt | |
| 6,770,089 B1 | 8/2004 | Hong et al. | |
| 6,818,013 B2 | 11/2004 | Mitelberg | |
| 6,833,003 B2 | 12/2004 | Jones | |
| 6,899,914 B2 | 5/2005 | Schaldach | |
| 6,911,040 B2 | 6/2005 | Johnson et al. | |
| 6,918,928 B2 | 7/2005 | Wolinsky | |
| 6,929,659 B2 | 8/2005 | Pinchuk | |
| 6,945,994 B2 | 9/2005 | Austin et al. | |
| 6,955,685 B2 | 10/2005 | Escamilla | |
| 6,960,227 B2 | 11/2005 | Jones | |
| 6,960,228 B2 | 11/2005 | Mitelberg et al. | |
| 6,970,734 B2 | 11/2005 | Eidenschink | |
| 7,001,422 B2 | 2/2006 | Escamilla | |
| 7,037,331 B2 | 5/2006 | Mitelberg | |
| 7,122,052 B2 | 10/2006 | Greenhaigh | |
| 7,201,769 B2 | 4/2007 | Jones et al. | |
| 7,208,008 B2 | 4/2007 | Clarke | |
| 7,267,685 B2 | 9/2007 | Butaric | |
| 7,288,111 B1 | 10/2007 | Holloway et al. | |
| 7,291,167 B2 | 11/2007 | DiCaprio | |
| 7,309,351 B2 | 12/2007 | Escamilla et al. | |
| 7,344,559 B2 | 3/2008 | Gray | |
| 7,462,190 B2 | 12/2008 | Lombardi | |
| 7,480,973 B2 | 1/2009 | Miller | |
| 7,628,806 B2 | 12/2009 | Yampolsky et al. | |
| 7,632,302 B2 | 12/2009 | Vreeman et al. | |
| 7,641,647 B2 | 1/2010 | Gunderson | |
| 7,655,031 B2 | 2/2010 | Tenne et al. | |
| 7,655,034 B2 | 2/2010 | Mitchell et al. | |
| 7,708,773 B2 | 5/2010 | Pinchuk et al. | |
| 7,758,629 B2 | 7/2010 | Holloway et al. | |
| 7,761,138 B2 | 7/2010 | Wang | |
| 7,806,919 B2 | 10/2010 | Bloom et al. | |
| 7,806,923 B2 | 10/2010 | Moloney | |
| RE42,244 E | 3/2011 | Boatman | |
| 7,913,371 B2 | 3/2011 | Klocke | |
| 7,985,213 B2 | 7/2011 | Parker | |
| 7,998,187 B2 | 8/2011 | Hartley et al. | |
| 8,021,418 B2 | 9/2011 | Gerberding | |
| 3,043,353 A1 | 10/2011 | Kaufmann et al. | |
| 8,043,357 B2 | 10/2011 | Hartley | |
| 8,048,139 B2 | 11/2011 | Frid et al. | |
| 8,092,510 B2 | 1/2012 | Metcalf et al. | |
| 8,142,456 B2 | 3/2012 | Rosqueta | |
| 8,152,833 B2 | 4/2012 | Zaver | |
| 8,182,523 B2 | 5/2012 | Tenne et al. | |
| 8,187,316 B2 | 5/2012 | Kuppurathanam | |
| 8,357,194 B2 | 1/2013 | Majercak | |
| 8,372,133 B2 | 2/2013 | Douk et al. | |
| 8,394,119 B2 | 3/2013 | Zaver | |
| 8,449,600 B2 | 5/2013 | Hartley et al. | |
| 8,562,666 B2 | 10/2013 | Bonsignore | |
| 8,579,959 B2 | 11/2013 | Ducke | |
| 8,597,276 B2 | 12/2013 | Vongphakdy et al. | |
| 8,641,748 B2 | 2/2014 | Hebert et al. | |
| 8,672,992 B2 | 3/2014 | Orr | |
| 8,709,065 B2 | 4/2014 | Chobotov | |
| 8,734,501 B2 | 5/2014 | Hartley et al. | |
| 8,778,008 B2 | 7/2014 | Amplatz et al. | |
| 8,816,247 B1 | 8/2014 | Janardhan et al. | |
| 8,864,811 B2 | 10/2014 | Kao | |
| 9,078,731 B2 | 7/2015 | Mortarino | |
| 9,301,864 B2 | 4/2016 | Kao | |
| 9,320,590 B2 * | 4/2016 | Zaver | A61F 2/01 |
| 9,339,260 B2 | 5/2016 | Eidenschink et al. | |
| 9,427,343 B2 | 8/2016 | Bogert | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |

(56) References Cited

U.S. PATENT DOCUMENTS

| | | |
|---|---|---|
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,713,523 B2 | 7/2017 | Zacharias |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,787,260 B2 | 10/2017 | Lehtola |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 10,076,428 B2 | 9/2018 | Gorochow |
| 10,206,796 B2 | 2/2019 | Tehrani et al. |
| 2001/0021873 A1 | 9/2001 | Stinson |
| 2001/0025195 A1 | 9/2001 | Shaolian |
| 2001/0049554 A1 | 12/2001 | Ruiz et al. |
| 2002/0095205 A1 | 7/2002 | Edwin |
| 2002/0111671 A1 | 8/2002 | Stenzel |
| 2002/0151953 A1 | 10/2002 | Chobotov |
| 2002/0151956 A1 | 10/2002 | Chobotov |
| 2002/0188344 A1 | 12/2002 | Bolea |
| 2002/0198587 A1 | 12/2002 | Greenberg et al. |
| 2003/0009211 A1 | 1/2003 | DiCarlo |
| 2003/0055493 A1 | 3/2003 | Carpenter |
| 2003/0114922 A1 | 6/2003 | Iwasaka |
| 2003/0144725 A1 | 7/2003 | Lombardi |
| 2003/0225448 A1 | 12/2003 | Gerberding |
| 2004/0015229 A1 | 1/2004 | Fulkerson |
| 2004/0024416 A1 | 2/2004 | Yodfat et al. |
| 2004/0044399 A1 | 3/2004 | Ventura |
| 2004/0073291 A1 | 4/2004 | Brown |
| 2004/0167619 A1 | 8/2004 | Case |
| 2004/0236406 A1 | 11/2004 | Gregorich |
| 2004/0254637 A1 | 12/2004 | Yang |
| 2005/0010281 A1 | 1/2005 | Yodfat et al. |
| 2005/0033406 A1 | 2/2005 | Barnhart |
| 2005/0043784 A1 | 2/2005 | Yampolsky et al. |
| 2005/0049668 A1 | 3/2005 | Jones et al. |
| 2005/0049669 A1 | 3/2005 | Jones et al. |
| 2005/0049670 A1 | 3/2005 | Jones |
| 2005/0125051 A1 | 6/2005 | Eidenschink |
| 2005/0131516 A1 | 6/2005 | Greenhalgh |
| 2005/0148866 A1 | 7/2005 | Gunderson |
| 2005/0234536 A1 | 10/2005 | Mitelberg |
| 2005/0257674 A1 | 11/2005 | Nishri et al. |
| 2005/0283220 A1 | 12/2005 | Gobran |
| 2005/0288775 A1 | 12/2005 | Dong |
| 2006/0015173 A1 | 1/2006 | Clifford |
| 2006/0064156 A1 | 3/2006 | Thistle |
| 2006/0069424 A1 | 3/2006 | Acosta |
| 2006/0195175 A1 | 8/2006 | Bregulla |
| 2006/0212113 A1 | 9/2006 | Shaolian et al. |
| 2006/0271153 A1 | 11/2006 | Garcia |
| 2006/0287717 A1 | 12/2006 | Rowe |
| 2007/0005127 A1 | 1/2007 | Boekstegers |
| 2007/0043432 A1 | 2/2007 | Perouse |
| 2007/0060994 A1 | 3/2007 | Gobran |
| 2007/0100427 A1 | 5/2007 | Perouse |
| 2007/0156230 A1 | 7/2007 | Dugan |
| 2007/0167955 A1 | 7/2007 | Arnault De La Menardiere et al. |
| 2007/0191922 A1 | 8/2007 | Hartley |
| 2007/0203503 A1 | 8/2007 | Salahieh |
| 2007/0208373 A1 | 9/2007 | Zaver et al. |
| 2007/0213810 A1 | 9/2007 | Newhauser |
| 2007/0219612 A1 | 9/2007 | Andreas |
| 2007/0219613 A1 | 9/2007 | Kao |
| 2007/0233223 A1 | 10/2007 | Styrc |
| 2007/0233224 A1 | 10/2007 | Leynov |
| 2007/0238979 A1 | 10/2007 | Huynh |
| 2007/0255385 A1 | 11/2007 | Tenne et al. |
| 2008/0009934 A1 | 1/2008 | Schneider et al. |
| 2008/0009938 A1 | 1/2008 | Huang |
| 2008/0071307 A1 | 3/2008 | DeBruyne et al. |
| 2008/0140172 A1 | 6/2008 | Carpenter |
| 2008/0221664 A1 | 9/2008 | Bales et al. |
| 2008/0221670 A1 | 9/2008 | Clerc |
| 2008/0243227 A1 | 10/2008 | Lorenzo |
| 2008/0288046 A1 | 11/2008 | Hemerick |
| 2009/0005848 A1 | 1/2009 | Strauss |
| 2009/0030501 A1 | 1/2009 | Morris |
| 2009/0076594 A1 | 3/2009 | Sabaria |
| 2009/0082844 A1 | 3/2009 | Zacharias |
| 2009/0082845 A1 | 3/2009 | Chobotov |
| 2009/0082847 A1 | 3/2009 | Zacharias |
| 2009/0163951 A1 | 6/2009 | Simmons |
| 2009/0192588 A1 | 7/2009 | Shin |
| 2009/0198315 A1 | 8/2009 | Boudjemline |
| 2009/0234429 A1 | 9/2009 | Lau |
| 2009/0248133 A1 | 10/2009 | Bloom |
| 2009/0287145 A1 | 11/2009 | Cragg |
| 2009/0306761 A1 | 12/2009 | Hebert et al. |
| 2009/0326640 A1 | 12/2009 | Yoshimura |
| 2010/0010619 A1 | 1/2010 | Tischler |
| 2010/0010622 A1 | 1/2010 | Lowe |
| 2010/0069948 A1 | 3/2010 | Veznedaroglu |
| 2010/0161028 A1 | 6/2010 | Chuter |
| 2010/0161036 A1 | 6/2010 | Pintor |
| 2010/0234935 A1 | 9/2010 | Bashiri |
| 2010/0274282 A1* | 10/2010 | Olson ............... A61L 17/04 606/228 |
| 2010/0292777 A1 | 11/2010 | Meyer |
| 2010/0298872 A1* | 11/2010 | Berndt ............ A61B 17/06166 606/228 |
| 2010/0324651 A1 | 12/2010 | Holzer |
| 2010/0331972 A1 | 12/2010 | Pintor |
| 2011/0004237 A1 | 1/2011 | Schneider et al. |
| 2011/0184508 A2 | 7/2011 | Burmeister |
| 2011/0264186 A1 | 10/2011 | Berglung et al. |
| 2011/0307049 A1 | 12/2011 | Kao |
| 2012/0035714 A1 | 2/2012 | Ducke et al. |
| 2012/0041538 A1 | 2/2012 | White |
| 2012/0168022 A1 | 7/2012 | Rasmussen |
| 2012/0191176 A1 | 7/2012 | Nagl |
| 2012/0197377 A1 | 8/2012 | Diller |
| 2012/0271403 A1 | 10/2012 | Gries |
| 2013/0041454 A1 | 2/2013 | Dobson |
| 2013/0060323 A1 | 3/2013 | McHugo |
| 2013/0123901 A1 | 5/2013 | Connor |
| 2013/0144375 A1 | 6/2013 | Giasolli |
| 2013/0245745 A1 | 9/2013 | Vong et al. |
| 2013/0253572 A1 | 9/2013 | Molaei et al. |
| 2013/0274849 A1 | 10/2013 | Zaver |
| 2013/0345739 A1 | 12/2013 | Brady |
| 2014/0025161 A1 | 1/2014 | Stankus et al. |
| 2014/0200648 A1 | 7/2014 | Newell et al. |
| 2014/0277332 A1 | 9/2014 | Slazas et al. |
| 2014/0277360 A1 | 9/2014 | Gimary et al. |
| 2014/0277376 A1 | 9/2014 | Lorenzo |
| 2014/0277400 A1 | 9/2014 | Wainwright et al. |
| 2014/0336741 A1 | 11/2014 | Connor |
| 2015/0045831 A1* | 2/2015 | Allen ................ A61F 2/0811 606/228 |
| 2015/0119974 A1 | 4/2015 | Rothstein |
| 2015/0148882 A1 | 5/2015 | Ma et al. |

(56) References Cited

U.S. PATENT DOCUMENTS

| | | |
|---|---|---|
| 2015/0265400 A1 | 9/2015 | Eidenschink |
| 2015/0320556 A1 | 11/2015 | Levi |
| 2015/0374483 A1 | 12/2015 | Janardham et al. |
| 2016/0030155 A1 | 2/2016 | Cox et al. |
| 2016/0038280 A1 | 2/2016 | Morriss |
| 2016/0058524 A1 | 3/2016 | Tehrani et al. |
| 2016/0235561 A1 | 8/2016 | Wrobel et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero |
| 2017/0079680 A1 | 3/2017 | Bowman |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079813 A1 | 3/2017 | Bar et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0156734 A1 | 6/2017 | Griffin |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0196689 A1 | 7/2017 | Salahieh |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265870 A1 | 9/2017 | Kealey et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281375 A1 | 10/2017 | Longo |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0290686 A1 | 10/2017 | Sirhan |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0092766 A1 | 4/2018 | Gorochow |
| 2018/0263794 A1 | 9/2018 | Slazas et al. |
| 2018/0333281 A1 | 11/2018 | Tehrani et al. |
| 2019/0015229 A1 | 1/2019 | Fukutaki |
| 2019/0021888 A1* | 1/2019 | Tehrani ............ A61F 2/07 |
| 2019/0053899 A1 | 2/2019 | Levi |
| 2019/0224008 A1 | 7/2019 | Bressloff |

FOREIGN PATENT DOCUMENTS

| | | |
|---|---|---|
| CN | 103347466 A | 10/2013 |
| DE | 202008014828 U1 | 2/2009 |
| DE | 102011015995 A1 | 10/2012 |
| EP | 0894505 A2 | 2/1999 |
| EP | 1488763 A2 | 12/2004 |
| EP | 1634546 A1 | 3/2006 |
| EP | 2545887 A1 | 2/2009 |
| EP | 2 777 642 A1 | 9/2014 |
| EP | 3 311 782 A1 | 4/2018 |
| JP | 11-57010 A | 3/1999 |
| JP | 11-57020 A | 3/1999 |
| WO | 01/35864 A1 | 5/2001 |
| WO | WO 2001058384 | 8/2001 |
| WO | WO 2001072240 A1 | 10/2001 |
| WO | 2008/130530 A1 | 10/2008 |
| WO | 2018/082440 A1 | 6/2012 |

OTHER PUBLICATIONS

MITCALE.Com; Welded connections excerpt, downloaded Dec. 6, 2012.

Plug Weld Joining Two Plates; Excerpt from esabna.com, downloaded Dec. 6, 2012.

Navigate Tough Anatomy; brochure Copyright 2009; Codman & Shurtleff, Inc., 325 Paramount Drive, Raynham, Massachusetts.

Office Action and Search Report issued for corresponding Chinese Application No. 201510535841.7 dated Apr. 8, 2018.

Search Report issued for corresponding Chinese Application No. 201510535841.7 dated Nov. 30, 2018.

Extended European Search Report issued in corresponding European Patent Application No. 19 21 9438 dated Apr. 7, 2020.

* cited by examiner

METHOD OF MAKING A MULTI-STRAND IMPLANT WITH ENHANCED RADIOPACITY

CROSS REFERENCE TO RELATED APPLICATIONS

This application is a divisional of U.S. application Ser. No. 14/469,862, entitled "Multi-strand implant with enhanced radiopacity" and filed Aug. 8, 2014, the contents of which are incorporated herein by reference as if set forth verbatim.

BACKGROUND OF THE INVENTION

Field of the Invention

The invention relates to implants within body vessels and more particularly to flow diverters, stents and other implants formed of strands of material and having radiopaque properties.

Description of the Related Art

Vascular disorders and defects such as aneurysms and other arterio-venous malformations are especially difficult to treat when located near critical tissues or where ready access to a malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

A number of vaso-occlusive devices have been formed of helical windings or coils of metallic wires, braided fibers, and/or woven fibers. Implants formed of non-metallic fibers, or of other materials having a low radiodensity, are difficult to track during insertion through vasculature, placement at a selected site, and possible subsequent recovery. Radiopaque fibers have been added to implants such as described by Engelson et al. in U.S. Pat. No. 5,423,849. However, the diameter of the radiopaque fibers often is very small, typically between 0.0005 to 0.005 inches, and single strands of these fibers are difficult to see during imaging by fluoroscopy or other viewing techniques. Radiopaque materials include platinum, chromium, cobalt, tantalum, tungsten, gold, silver, and alloys thereof.

Depending on the level of radiopacity desired, several techniques are known to increase visibility of an implant during imaging. Additional strands of radiopaque materials are added to the implant, the diameter of the individual strands is increased, and/or the volume of the radiopaque material is increased, such as by forming a coil. However, adding additional strands of radiopaque material may change the mechanical performance of the implant, especially for implants utilizing strands made of shape memory alloy such as Nickel Titanium. Increasing the diameter of the individual radiopaque strands for the implant not only potentially impacts the mechanical performance of the implant but also increases the wall thickness of the implant. Likewise, increasing the volume of radiopaque material by winding the radiopaque filament into a coil and adding it to the implant will impact both the mechanical performance of the implant as well as the thickness of the implant wall.

A composite yarn to reinforce a textile prosthesis is disclosed by Dong in US Patent Publication 2005/0288775. Blood flow diverters which may include braided sections are described by Gobran et al. in US Patent Publication No. 2007/0060994. Stents having radiopaque mesh to serve as filters are presented in U.S. Pat. No. 8,394,119 by Zaver et al. A woven fabric having composite yarns for endoluminal devices is described by Rasmussen et al. in US 2012/0168022.

Another type of vaso-occlusive device is illustrated in U.S. Pat. No. 5,645,558 by Horton as having one or more strands of flexible material which are wound to form a generally spherical or ovoid vaso-occlusive structure when relaxed after being placed in a vascular cavity such as an aneurysm or fistula. Similarly, U.S. Pat. No. 5,916,235 by Guglielmi cites earlier patents describing detachable coils and then discloses an expandable cage as a vaso-occlusive structure that can receive and retain one or more embolic coils after the cage is expanded within an aneurysm. A self-expandable aneurysm filling device is disclosed in US Patent Publication No. 2010/0069948 by Veznedaroglu et al.

Typically, a stent-like vascular reconstruction device is first guided beneath the aneurysm to be treated using a delivery catheter. One commercially available reconstruction product is the CODMAN ENTERPRISE® Vascular Reconstruction Device and System as described, for example, in a Navigate Tough Anatomy brochure Copyright 2009 by Codman & Shurtleff, Inc., 325 Paramount Drive, Raynham, Mass. The CODMAN ENTERPRISE® stent device is carried by a central delivery wire and initially held in place on the delivery wire in a collapsed state by a sheath-type introducer. Typically, a delivery catheter such as a PROWLER® SELECT® Plus microcatheter, also commercially available from Codman & Shurtleff and as disclosed by Gore et al. in U.S. Pat. No. 5,662,622, for example, is first positioned intravascularly with its distal tip slightly beyond the neck of the aneurysm. The tapered distal tip of the introducer is mated with the proximal hub of the delivery catheter, and the delivery wire is then advanced through the delivery catheter.

The CODMAN ENTERPRISE® stent device has a highly flexible, self-expanding closed cell design with a number of coils of radiopaque wire to serve as markers at each flared end of the device, similar to the stent illustrated in the published patent application by Jones et al., cited above. Manufacture of such markers is relatively time-consuming and expensive due to the small size of the stent and the need to wrap the radiopaque wire multiple times around struts on the stent, which is especially difficult within closed cells of the stent.

It is therefore desirable to increase radiopacity of an implant in a cost-effective manner while minimizing impacts to implant performance.

SUMMARY OF THE INVENTION

An object of the present invention is increase radiopacity of an implant having a plurality of strands while minimizing changes to implant manufacturing processes.

Another object of the present invention is to enhance radiopacity without adversely affecting performance of the implant.

A still further object of the invention is to increase radiopacity while minimizing impacts to the mechanical properties of the implant and maintaining similar wall thickness.

This invention results from the realization that two or more strands of radiopaque material can be placed side-by-side on a single carrier as a multi-strand, which can be handled in the same manner as a single strand during manufacture of an implant.

This invention features an implant for medical use, including a structure having a body, the body constructed to include a plurality of single strands composed of at least a first material. The body further includes at least one multi-strand of radiopaque material incorporated among the single strands, the multi-strand having at least two side-by-side filaments of radiopaque material that lie substantially contiguous to each other over substantially the entire length of the multi-strand.

In some embodiments, each of the side-by-side filaments of the multi-strand is a monofilament of radiopaque material. Preferably, the diameter of each side-by-side filament is substantially the same as the diameter of the single strands.

This invention also features an implant having a body wall formed of a plurality of single strands of a first material establishing a first spacing pattern and a first wall thickness, such as an open braid or open weave pattern in a substantially tubular shape. The body wall further includes a plurality of multi-strands of radiopaque material interspersed with the single strands, each multi-strand having at least two side-by-side filaments of radiopaque material that lie substantially contiguous to each other, and each multi-strand joining in the first spacing pattern without substantial deviation from that pattern and without substantially altering the first wall thickness.

This invention further features a method for manufacturing an implant for medical use, including providing a plurality of carriers, each carrier having a single strand of a first material, and providing at least one carrier having a multi-strand of radiopaque material, the multi-strand having at least two side-by-side filaments of radiopaque material that lie substantially contiguous to each other over substantially the entire length of the multi-strand. The method further includes forming a body for the implant, preferably having a substantially constant wall thickness, utilizing both the single strands and the multi-strand.

In some embodiments, the carrier having the multi-strand is substantially the same as the carriers for the single strands. Each of the side-by-side filaments of the multi-strand is a monofilament of radiopaque material. Preferably, the diameter of each side-by-side filament is substantially the same as the diameter of the single strands. In a number of embodiments, forming the body includes establishing a first spacing pattern, and each multi-strand joins in the first spacing pattern without substantial deviation from that pattern. In certain embodiments, the first spacing pattern is one of an open braid pattern and an open weave pattern. In some embodiments, at least one multi-strand carrier is utilized for every dozen single-strand carriers, such as the machine having at least 42 carriers, and at least 6 of the carriers are loaded with the multi-strands of radiopaque material.

This invention also features a method of retro-fitting an implant forming machine having a plurality of carriers, each carrier designed to carry a single strand composed of at least one of a first material and a radiopaque material. The method includes selecting at least one of the plurality of carriers and loading the selected carrier with a multi-strand of radiopaque material. The multi-strand has at least two side-by-side filaments of radiopaque material that lie substantially contiguous to each other over substantially the entire length of the multi-strand. The method further includes forming a body for the implant utilizing both the single strands and the one or more multi-strands of radiopaque material.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by an implant for medical use, and method of making same, including a structure having a body constructed at least in part with a plurality of single strands composed of a first material. The body further includes at least one multi-strand of radiopaque material incorporated among the single strands, the multi-strand having at least two side-by-side filaments of radiopaque material that are in parallel with each other, that is, the filaments lie substantially contiguous to each other over substantially the entire length of the multi-strand. Suitable implants include flow diverters, stents, filters, surgical mesh, and other implants or portions thereof formed of strands of material and benefiting from enhanced radiopaque properties.

The term "strand" is intended in its broadest meaning to include a wire, a fiber, a filament, or other single elongated member. The term "radiopaque" is utilized for its normal meaning of being radiodense, that is, formed of one or more materials which inhibit the passage of electromagnetic radiation to increase visibility during imaging. Suitable radiopaque materials for use according to the present invention include platinum, chromium, cobalt, tantalum, tungsten, gold, silver, and alloys thereof.

Figure 1:
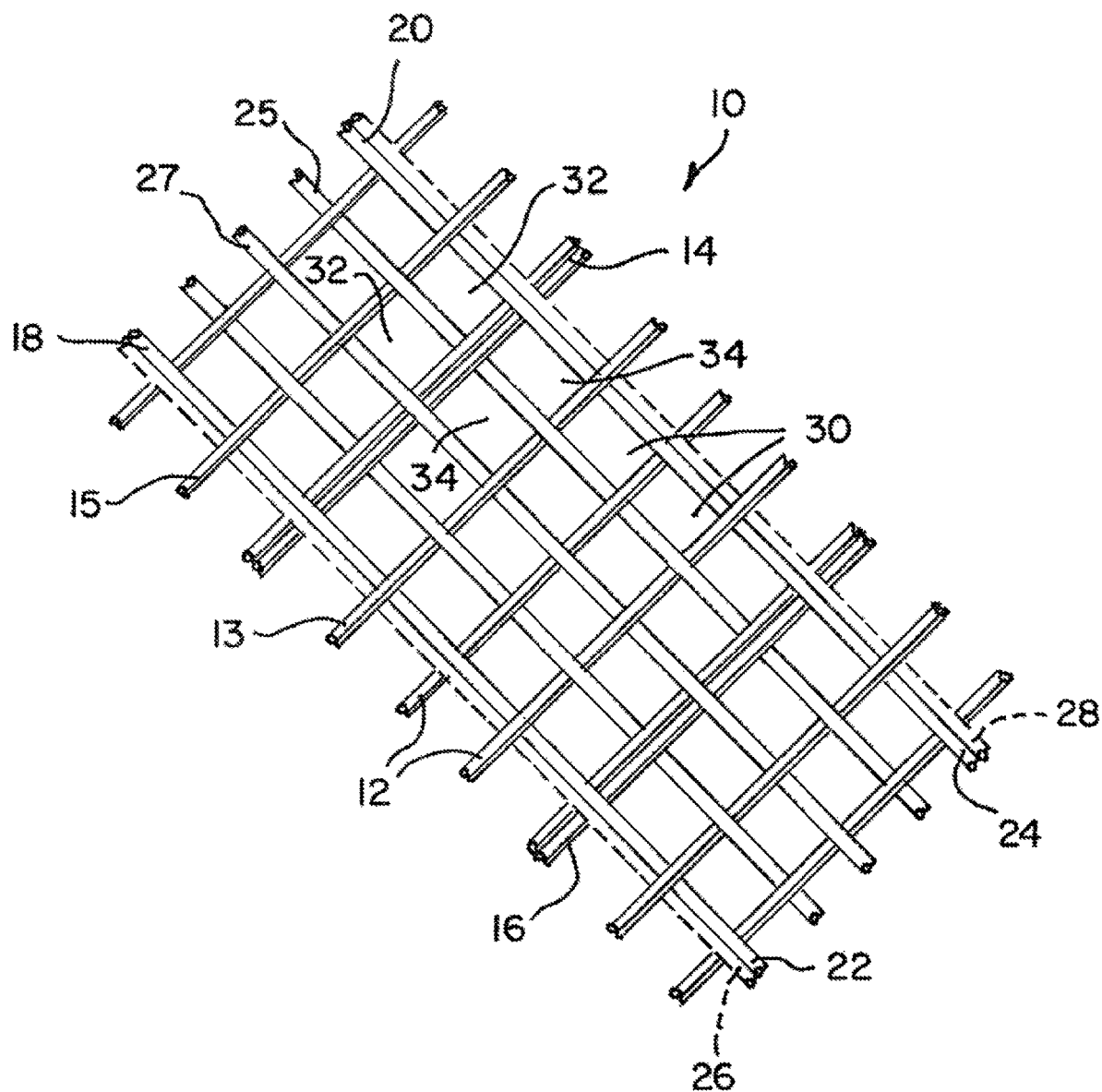
FIG. 1 is a schematic enlarged view of a portion of an implant body formed of single strands and one or more radiopaque multi-strands according to the present invention.

FIG. 1 is a schematic enlarged view of a portion of an implant body 10 according to the present invention formed of single strands 12 composed of at least a first material and one or more radiopaque multi-strands 14. In this construction, body 10 is woven to include at least a second multi-strand 16. In another construction, indicated by dashed lines, the body 10 further includes multi-strands 18 and 20 formed of monofilaments 22 and 24 each laid together with monofilaments 26 and 28, respectively.

The pattern of body 10, which is woven in some constructions and braided in other constructions, includes openings 30 defined by single strands 12 oriented in a first direction and by single strands 24 and 25 oriented in a second direction that is transverse to the first direction, for example. Body 10 further includes openings 32 and 34 defined on either side of multi-strand 14 by single strands 13 and 15 oriented in the same direction as multi-strand 14 and by single strands 24, 25 and 27 oriented in a transverse direction. In some constructions, openings 32 and 34 are slightly larger than openings 30 which are defined only by single strands; in other constructions, all openings 30, 32 and 34 are substantially the same. All of these constructions are considered to have substantially the same pattern as if body 10 were formed solely from single strands of material.

Since the multi-strands are braided, woven or otherwise laid in parallel to each other in the same manner as if single strands of radiopaque material were utilized, and especially when each filament of the multi-strand has the same diameter as the single strands, there is little or no mechanical impact to the performance of the implant, such as flexibility, ability to expand, and crimped profile.

Figure 2:
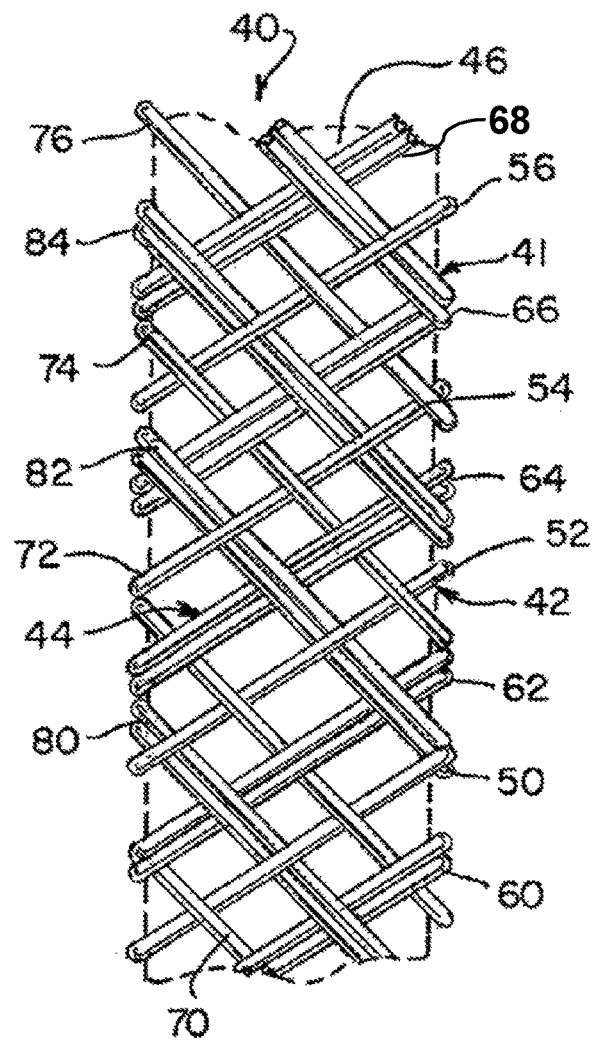
FIG. 2 is a schematic side view of a tubular braided implant having alternating single and multi-strands according to the present invention.

Tubular braided implant 40, FIG. 2, is a substantially cylindrical, hollow and porous structure such as a stent or a flow diverter having a body 41 formed of alternating single strands 42 and multi-strands 44 according to one construction of the present invention. Body 41 defines a central lumen 46. Single strands 50, 52, 54 and 56 are visible as oriented in a first direction and alternating with multi-strands 60, 62, 64, 66 and 68. Single strands 70, 72, 74 and 76 are visible as oriented in a second direction and alternating with multi-strands 80, 82 and 84. In some constructions, two or more of the separately numbered single strands are actually different portions of a single, continuous single strand as will be readily apparent to one of ordinary skill in the braiding and weaving art. Similarly, two or more of the separately numbered multi-strands are actually different portions of a single, continuous multi-strand.

Figure 3:
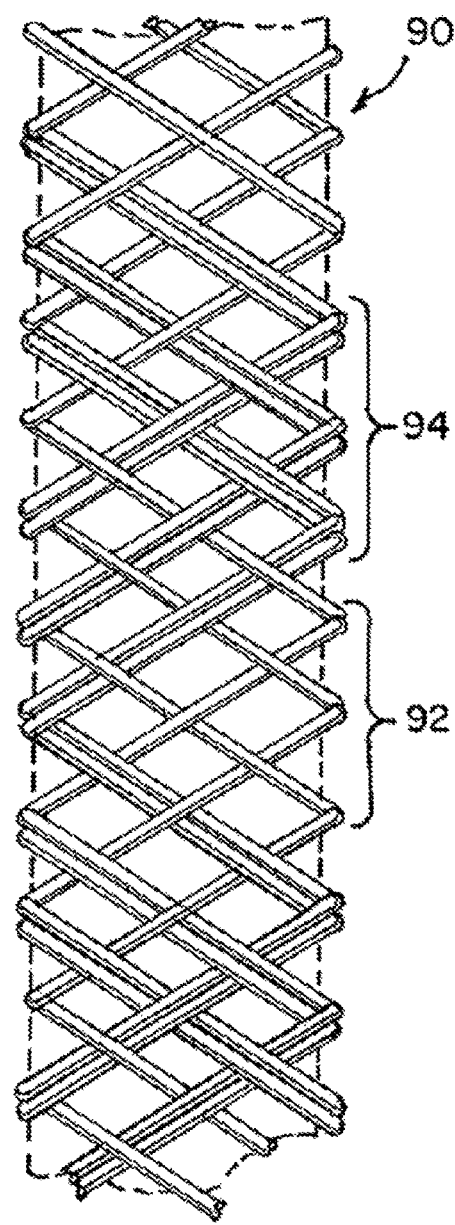
FIG. 3 is a schematic side view of a tubular braided implant having a more complex pattern of single and multi-strands according to the present invention.

FIG. 3 is a schematic side view of an alternative tubular braided implant 90 having a more complex pattern of three single strands 92 alternating with three multi-strands 94 according to another construction of the present invention. When viewed in a patient utilizing fluoroscopy or other imaging technique, implants 40 and 90 each will generate a different image, which aids a surgeon or other user to distinguish it from other implants and anatomical features. In some constructions, implants 40 and/or 90 define inner lumens ranging from 2.0 mm to approximately 5.0 mm in diameter.

This invention may also be accomplished by a method for manufacturing an implant for medical use, including providing a plurality of carriers, each carrier having a single strand of a first material, and providing at least one carrier having a multi-strand of radiopaque material, the multi-strand having at least two side-by-side filaments of radiopaque material that lie substantially contiguous to each other over substantially the entire length of the multi-strand. The method further includes forming a body for the implant, preferably having a substantially constant wall thickness, utilizing both the single strands and the multi-strand.

Figure 4:
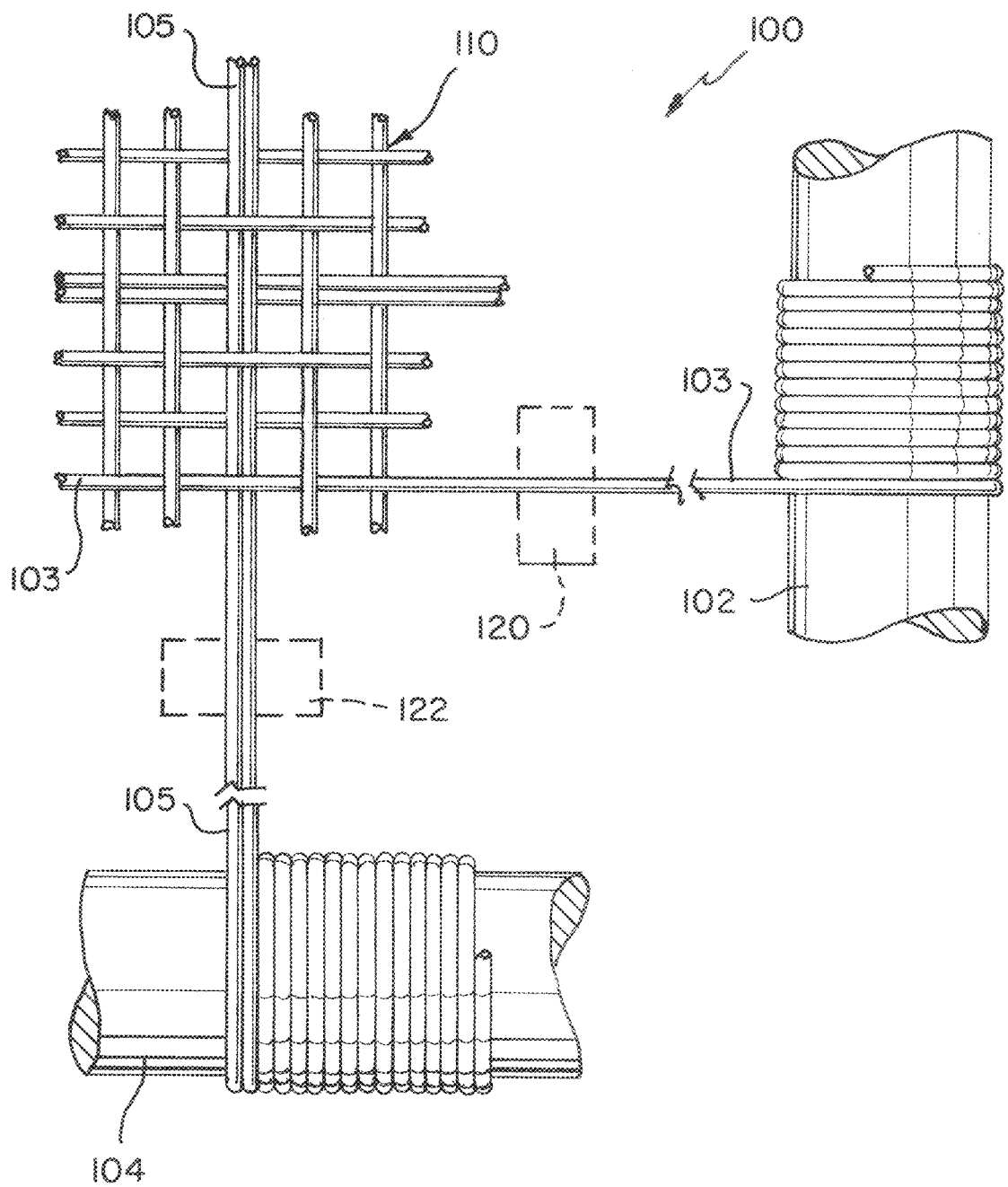
FIG. 4 is a schematic diagram a portion of an implant forming machine including a conventional carrier providing a radiopaque multi-strand during manufacture of an implant according to the present invention.

FIG. 4 is a schematic diagram, not to scale, of a portion of an implant forming machine 100 including conventional single-strand carriers 102 and 104 shown during manufacture of an implant 110 according to the present invention. Carrier 102 is loaded with single strand 103 while carrier 104 is loaded with a radiopaque multi-strand 105. Dashed components 120 and 122 represent conventional mechanisms for directing single strand 103 and multi-strand 105, respectively, to form implant 110 as will be understood by those of ordinary skill in the relevant field.

For ease of illustration, the pattern of strands shown in FIGS. 1-4 is a 1-over-1 braid-type pattern. As will also be understood by those of ordinary skill after studying the present disclosure, other braid, knit, or weave patterns can be utilized according to the present invention, such as 1-over-2, 2-over-2, and other known patterns. Tension placed on each strand during implant formation is adjusted according to conventional techniques.

Another technique according to the present invention is to retro-fit an implant forming machine having a plurality of carriers such as carriers 102 and 104, each carrier designed to carry a single strand composed of at least one of a first material and a radiopaque material. The technique includes selecting at least one of the plurality of carriers, such as carrier 104, and loading the selected carrier with a multi-strand of radiopaque material. The multi-strand has at least two side-by-side filaments of radiopaque material that lie substantially contiguous to each other over substantially the entire length of the multi-strand. A body is formed for the implant utilizing both the single strands and the multi-strand.

In preferred techniques, each of the side-by-side filaments of the multi-strand is a monofilament of radiopaque material. In one construction, the carrier having the multi-strand is substantially the same as the carriers for the single strands. Each of the side-by-side filaments of the multi-strand is a monofilament of radiopaque material. Preferably, the diameter of each side-by-side filament is substantially the same as the diameter of the single strands. Forming the body includes establishing a first spacing pattern, such as an open braid pattern or an open weave pattern, and a first wall thickness, and each multi-strand joins in the first spacing pattern without substantial deviation from that pattern and without substantially altering the first wall thickness.

In certain techniques, at least one multi-strand carrier is utilized for every dozen single-strand carriers. Some machines have at least 42 carriers, such as 48 carriers, and at least 6 of the carriers, such as 8 carriers, are loaded with the multi-strands of radiopaque material. This still results in a 48-carrier braid but having double the number of radiopaque strands as when the 8 carriers are loaded with single strands of radiopaque material.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for manufacturing an implant for medical use, comprising:
   providing a plurality of carriers, each carrier having only a single strand composed of at least a first non-radiopaque material;
   providing at least one carrier having a multi-strand of radiopaque material, the multi-strand having at least two side-by-side filaments of radiopaque material that lie contiguous to each other over the entire length of the multi-strand; and
   forming a body for the implant utilizing both the single strands and the multi-strand.

2. The method of claim 1 wherein the carrier having the multi-strand is the same as the carriers for the single strands.

3. The method of claim 2 wherein each of the side-by-side filaments of the multi-strand is a monofilament of radiopaque material.

4. The method of claim 3 wherein forming the body includes establishing a first spacing pattern and a first wall thickness, and each multi-strand joins in the first spacing pattern without substantial deviation from that pattern and without altering the first wall thickness.

5. The method of claim 3 wherein the first spacing pattern is one of an open braid pattern and an open weave pattern.

6. The method of claim 3 wherein at least one multi-strand carrier is utilized for every dozen single-strand carriers.

7. The method of claim 1 wherein the first material is non-radiopaque.

8. The method of claim 1 wherein the step of providing at least one carrier having a multi-strand of radiopaque material further comprises providing the at least two side-by-side filaments with a diameter the same as a diameter of the single strand.

9. A method of retro-fitting an implant forming machine having a plurality of carriers, each carrier designed to carry only a single strand composed of at least one of a first non-radiopaque material and a radiopaque material, comprising:

selecting at least one of the plurality of carriers, each carrier designed to carry only the single strand, and loading the selected carrier with a multi-strand of radiopaque material, the multi-strand consisting of two side-by-side filaments of radiopaque material that lie contiguous to each other over the entire length of the multi-strand; and forming a body for the implant utilizing both the single strands and the multi-strand.

10. The method of claim 9 wherein each of the side-by-side filaments of the multi-strand is a monofilament of radiopaque material.

11. The method of claim 10 wherein forming the body includes establishing a first spacing pattern and a first wall thickness, and each multi-strand joins in the first spacing pattern without substantial deviation from that pattern and without altering the first wall thickness.

12. The method of claim 11 wherein the first spacing pattern is one of an open braid pattern and an open weave pattern.

13. The method of claim 12 wherein at least one multi-strand carrier is utilized for every dozen single-strand carriers.

14. The method of claim 13 wherein the machine has at least 42 carriers, and at least 6 of the carriers are loaded with the multi-strands of radiopaque material.

15. The method of claim 9 wherein the first material is non-radiopaque.

16. The method of claim 9 wherein the selecting step further comprises providing the at least two side-by-side filaments with a diameter the same as a diameter of the single strand.

* * * * *